United States Patent [19]
Barbara

[11] Patent Number: 5,217,481
[45] Date of Patent: Jun. 8, 1993

[54] SURGICAL INSTRUMENT

[76] Inventor: Mariano R. Barbara, Santiago Russiñol, 9, 07012 Palma De Mallorca, Spain

[21] Appl. No.: 757,202

[22] Filed: Sep. 10, 1991

[30] Foreign Application Priority Data

Sep. 21, 1990 [ES] Spain ................................. 9002765

[51] Int. Cl.$^5$ ............................................. A61M 29/00
[52] U.S. Cl. ....................................... 606/191; 606/85
[58] Field of Search ................... 606/85, 191; 29/76.4, 29/77, 78, 79

[56] References Cited

U.S. PATENT DOCUMENTS

| | | | |
|---|---|---|---|
| D. 273,806 | 5/1984 | Bolesky et al. | 606/85 |
| 4,587,964 | 5/1986 | Walker et al. | 606/85 |
| 4,625,725 | 12/1986 | Davison et al. | 606/85 |
| 5,006,121 | 4/1991 | Hafeli | 606/85 |

*Primary Examiner*—Edgar S. Burr
*Assistant Examiner*—Ren Yan
*Attorney, Agent, or Firm*—Young & Thompson

[57] ABSTRACT

A surgical instrument for dilatation and enlargement of the corpora cavernosa of the penis for use in surgical operations for the implantation of a penile prosthesis, the instrument having a mono-unit body of stainless steel and having two sectors including an operative sector and a handle sector, the operative sector having a substantially cylindrical configuration and being of considerable length with a slight curvature along its length forming a concave area on one side, the one side being smooth and slightly flattened, and a second side opposite the one side, the second side having ten longitudinal nerves arranged parallel to each other and in close proximity, and between which there are grooves which are also longitudinal, each of the nerves being provided with a longitudinal alignment of twelve uniformly distributed protuberances, each of the protuberances having a sawtooth shape including an oblique slanting planar surface which faces away from the handle sector, the end of the operative sector opposite to the handle sector being rounded, the operative sector of the body acting as a scraper, with the orientation of its protuberances facilitating penetration into the corpora cavernosa, and when pulled in the opposite direction out of the corpora cavernosa, carving furrows in the tissue of the corpora cavernosa.

1 Claim, 1 Drawing Sheet

SURGICAL INSTRUMENT

PURPOSE OF THE INVENTION

The present invention refers to a surgical instrument especially designed to facilitate the dilatation and enlargement of the span or inner diameter of the corpora cavernosa of the penis, in the surgical process of implantation of a penial prosthesis.

The instrument is useful in nearly all phases of implantation, and absolutely necessary when there is a fibrosis of corpora cavernosa.

BACKGROUND OF THE INVENTION

Certain diseases of the corpora cavernosa of the penis produce impotence or erectile disfunction which does not allow a normal erection, due to a sclerosis of the corpora cavernosa. On occasion, the correct and essential treatment consists in the implant of a penile prosthesis.

The surgical technique for the implantation of a penile prosthesis consists in all cases in the opening of both corpora cavernosa and the introduction into them of the mentioned prosthesis.

Previous to the introduction of the prosthesis it is necessary to dilate both corpora cavernosa to obtain an internal diameter which allows the prosthesis appropriate to the diameter or width of the penis before the disease to be introduced.

The dilation of the corpora cavernosa has until now been achieved with Hegar's instrument or scissors. In some cases, when the sclerosis is marked and quite advanced, the dilation with Hegar's instrument is almost impossible, and with scissors it is dangerous, as the pectiniform wall which separates the corpora cavernosa is easily perforated. There is also the danger of perforating the proximal or distal portion of the corpora cavernosa. Furthermore, neither the Hegar's instrument nor the scissors serve to increase the interior diameter of the corpora cavernosa, as they cannot remove tissue.

DESCRIPTION OF THE INVENTION

Specifically described, the surgical instrument is made up of a mono-unit body, preferently of stainless steel, of a basically cylindrical shape and a slightly curved trajectory, with a slight flattening of its concave area. One of its ends is rounded and the other extends into a handle that, in line with a preferent embodiment of the invention, can have a spatulous configuration, but can be given any other shape without detriment to the essential characteristics of the invention.

The mentioned cylindrical body is completely smooth in the sector opposite to its flattened and concave area, and the remaining face is occupied by a plurality of longitudinal nerves—generally a total of ten—separated by grooves or furrows that are also longitudinal. Each of these nerves has numerous small protuberances in the form of sawteeth. The instrument can therefore be used as a scraper that, as a result of the inclination of the mentioned jagged edges or protuberances, can be easily lodged in the recess of each of the corpora cavernosa of the penis. When the instrument is pulled contrariwise, furrows are carved in the cavernous tissues, thereby increasing their span. The smooth surface of the instrument, however, must be placed against the pectiniform wall seperating the two corpora cavernosa, so that this inner area of the bodies will remain unaffected by the scraping action of the instrument.

DESCRIPTION OF THE DRAWINGS

Following, a complete description is made of the mentioned surgical instrument as displayed in the attached drawings. These drawings show, as an example, a preferent embodiment of the instrument, although this is in no way limitative, since the instrument is susceptible of variations in respect of some of its features, provided these variations do not fundamentally alter its essential characteristics.

In the said drawings

Finally

PREFERENT EMBODIMENT OF THE INVENTION

Figures 1, 2A:
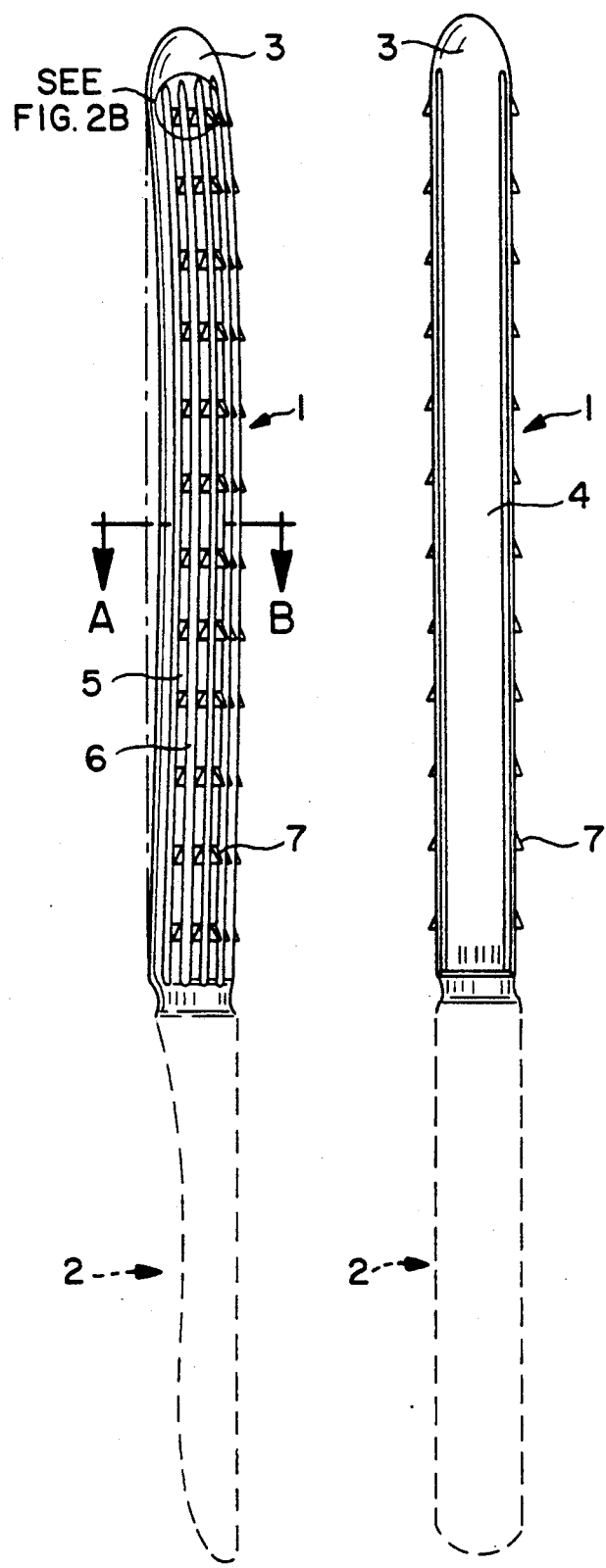
FIG. 1 is a lateral view of a surgical instrument designed in accordance with the present invention. What is here shown is its curved/concave and smooth side. The handle of the instrument has been drawn with a broken line, since its configuration is totally secondary and outside the scope of the invention.
FIG. 2A is another lateral view of the same instrument that is 90% out of phase in respect of the previous Figure. In this Figure the curvature of the body can be clearly appreciated.

After an examination of these Figures, it can be concluded that the surgical instrument that is envisaged, which could be called a 'cavernotome' consists of a mono-unit body of stainless steel with two sectors: an operative sector (1) and a handle or shaft (2) that can have the spatulous configuration represented in the Figures, a double-elbow configuration, or any other shape that may be deemed convenient, since this does not in any way affect the essential characteristics of the invention. The previously mentioned operative sector (1), which is basically cylindrical, presents a slight curvature, as can be especially observed in FIG. 2A, and is joined at one of its ends to the handle (2), with no break in continuity. The opposite end is topped by a rounded penetration point (3) that is roughly semi-ellipsoidal.

Figure 2B:
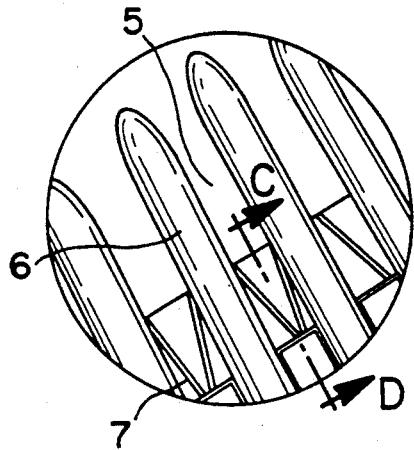
FIG. 2B is a view of the nerves and furrows in the body shown on a larger scale.
Figure 4:
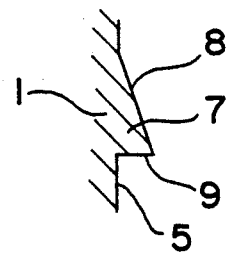
FIG. 4 is a longitudinal view of one of the sawtooth protuberances in the body, as per the enlarged C-D cross section of FIG. 2B.
Figure 3:
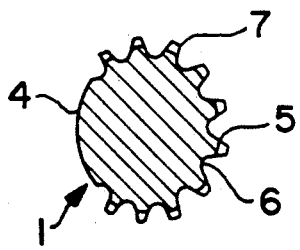
FIG. 3 is a cross-section of a specific feature of the instrument, as per the A-B cut line in FIG. 2A.

In this sector (1) of the instrument, and directly opposite its concave zone, a smooth area of the cylinder that constitutes the said body is slightly flattened. This affects, approximately, one fourth of its extension, while on the remaining surface there are numerous longitudinal nerves (5)—generally a total of ten—arranged parallely and in close proximity. These groups of nerves are separated by grooves (6) which are also longitudinal. The said longitudinal nerves (5) have numerous protuberances (7) with the shape of a rectangular pointed stem similar to a sawtooth, the profile of which can be clearly appreciated in FIG. 4. The layout of these protuberances is on an inclined plane (8) facing the extremity (3) of the instrument, in order to facilitate penetration in the recesses of the corpora cavernosa of the penis. Due to the fact that contrariwise to this inclined plane (8) is a straight grading (series of steps), the operative sector of the instrument can be employed in the manner of a scraper when, after introduction of the instrument in one of the corpora cavernosa, with its smooth sector (4) against the wall that seperates both corpora cavernosa, a traction is exerted on the handle (2) in the direction of the extraction of the instrument. This extraction does not entail any vacuum problems, since the grooves (6) arranged along the body (1) facilitate the penetration of air into the hollow interior of the corpora cavernosa.

In the example of practical embodiment shown in Figures, 12 protuberances have been provided to each one of the longitudinal nerves, and therefore the protuberances of the different longitudinal nerves also have, of their own, a transversal alignment. In this instance, as well, this number is only an example, since it can be increased or decreased without prejudice to the essential characteristics of the invention.

Based on this structuration, and for the purpose of adapting the surgical instrument to the specific requirements in each case, provision has been made for an ample range of variations. In the case of the body of the instrument (1) or operative sector, it can range between 115 and 250 mm, with widths of 9, 10, 11, 12 and 13 mm; there can also be variations in respect of the handle, as has been previously stated.

The form, dimensions and materials are also variable, and, in general, variations can be introduced in all that which is accessory or secondary, provided there is no change or modification in the essential character of the instrument described.

The terms employed in this specification are a true and precise reflection of the object described, and should always be considered from an ample viewpoint, rather than in a limitative way.

I claim:

1. A surgical instrument for dilatation and enlargement of the corpora cavernosa of the penis for use in surgical operations for the implantation of a penile prosthesis, said instrument having a mono-unit body of stainless steel and having two sectors including an operative sector and a handle sector, the operative sector having a substantially cylindrical configuration and being of considerable length with a slight curvature along its length forming a concave area on one side, the one side being smooth and slightly flattened, and a second side opposite said one side, said second side having ten longitudinal nerves arranged parallel to each other and in close proximity, and between which there are grooves which are also longitudinal, each of the nerves being provided with a longitudinal alignment of twelve uniformly distributed protuberances, each of the protuberances having a sawtooth shape including an oblique slanting planar surface which faces away from the handle sector, the end of the operative sector opposite to the handle sector being rounded, the operative sector of the body acting as a scraper, with the orientation of its protuberances facilitating penetration into the corpora cavernosa, and when pulled in the opposite direction out of the corpora cavernosa, carving furrows in the tissue of the corpora cavernosa.

* * * * *

UNITED STATES PATENT AND TRADEMARK OFFICE
CERTIFICATE OF CORRECTION

PATENT NO.   : 5,217,481
DATED        : June 8, 1993
INVENTOR(S)  : Mariano ROSSELLO BARBARA It is certified that error appears in the above-indentified patent and that said Letters Patent is hereby corrected as shown below:

On the title page:

In the heading of the patent, change "BARBARA" to --ROSSELLA BARBARA--;

In Item [76], Inventor: change "Mariano R. Barbara" to --Mariano Rossello Barbara--.

Signed and Sealed this

Twenty-second Day of April, 1997

*Attest:*

BRUCE LEHMAN

*Commissioner of Patents and Trademarks*

*Attesting Officer*